(12) United States Patent
Baek et al.

(10) Patent No.: US 9,387,775 B2
(45) Date of Patent: Jul. 12, 2016

(54) SYSTEM FOR CONTROLLING DRIVING OF ELECTRIC VEHICLE AND METHOD OF THE SAME

(71) Applicant: Samsung SDI Co., Ltd., Yongin-si, Gyeonggi-do (KR)

(72) Inventors: Woon-Seong Baek, Yongin-si (KR); Se-Jin Ji, Yongin-si (KR); Sang-Kyou Kim, Yongin-si (KR); Hyeon-Cheol Jeong, Yongin-si (KR)

(73) Assignee: Samsung SDI Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/677,671

(22) Filed: Apr. 2, 2015

(65) Prior Publication Data

US 2015/0283919 A1 Oct. 8, 2015

(30) Foreign Application Priority Data

Apr. 7, 2014 (KR) ........................ 10-2014-0041232

(51) Int. Cl.

| | |
|---|---|
| *B60L 9/00* | (2006.01) |
| *B60L 15/20* | (2006.01) |
| *B60L 11/18* | (2006.01) |
| *B60L 3/06* | (2006.01) |
| *B60L 3/12* | (2006.01) |
| *G06Q 30/02* | (2012.01) |
| *B60Q 9/00* | (2006.01) |
| *G01N 27/416* | (2006.01) |
| *A01D 69/02* | (2006.01) |

(52) U.S. Cl.
CPC ............... *B60L 15/2045* (2013.01); *B60L 3/06* (2013.01); *B60L 3/12* (2013.01); *B60L 11/1816* (2013.01); *B60L 11/1857* (2013.01); *B60L 11/1861* (2013.01); *A01D 69/02* (2013.01); *B60L 2240/12* (2013.01); *B60L 2240/547* (2013.01); *B60L 2240/549* (2013.01); *B60L 2240/622* (2013.01); *B60L 2250/16* (2013.01); *B60L 2260/52* (2013.01); *B60L 2260/54* (2013.01); *B60Q 9/00* (2013.01); *G01N 27/416* (2013.01); *G06Q 30/02* (2013.01); *Y02T 10/7258* (2013.01)

(58) Field of Classification Search
CPC ....... A01D 69/02; A01D 34/00; A01D 75/18; B60L 11/00; B60L 11/18; B60L 11/1822; B60L 11/1825; B60L 15/2045; B62M 6/40; G01N 27/41; G06Q 30/02; B60Q 9/00; G01C 21/3469

See application file for complete search history.

(56) References Cited

U.S. PATENT DOCUMENTS

| | | | |
|---|---|---|---|
| 2006/0284614 A1 | 12/2006 | Kim et al. | |
| 2012/0112754 A1* | 5/2012 | Kawai ................ | G01R 31/3651 324/428 |

(Continued)

FOREIGN PATENT DOCUMENTS

| | | |
|---|---|---|
| KR | 10-1998-0085363 A | 12/1998 |
| KR | 10-2004-0000724 A | 1/2004 |
| KR | 10-2006-0130509 A | 12/2006 |

*Primary Examiner* — Behrang Badii
(74) *Attorney, Agent, or Firm* — Knobbe, Martens, Olson & Bear, LLP

(57) ABSTRACT

A system for controlling driving of an electric vehicle including a motor and a method of the same are disclosed. In one aspect, the system includes a battery configured to output a driving current to the motor and a battery capacity calculator configured to determine the remaining battery capacity of the battery. The system also includes a controller configured to limit the driving current to a predetermined current limit value or less when the remaining battery capacity reaches a first predetermined value.

20 Claims, 2 Drawing Sheets

(56) References Cited

U.S. PATENT DOCUMENTS

2012/0159916 A1* 6/2012 Ishii ................ A01D 34/64
56/10.2 A

2012/0226441 A1* 9/2012 Willden ................ E01D 22/00
702/2

2013/0282472 A1* 10/2013 Penilla ................ B60L 11/1822
705/14.35

* cited by examiner

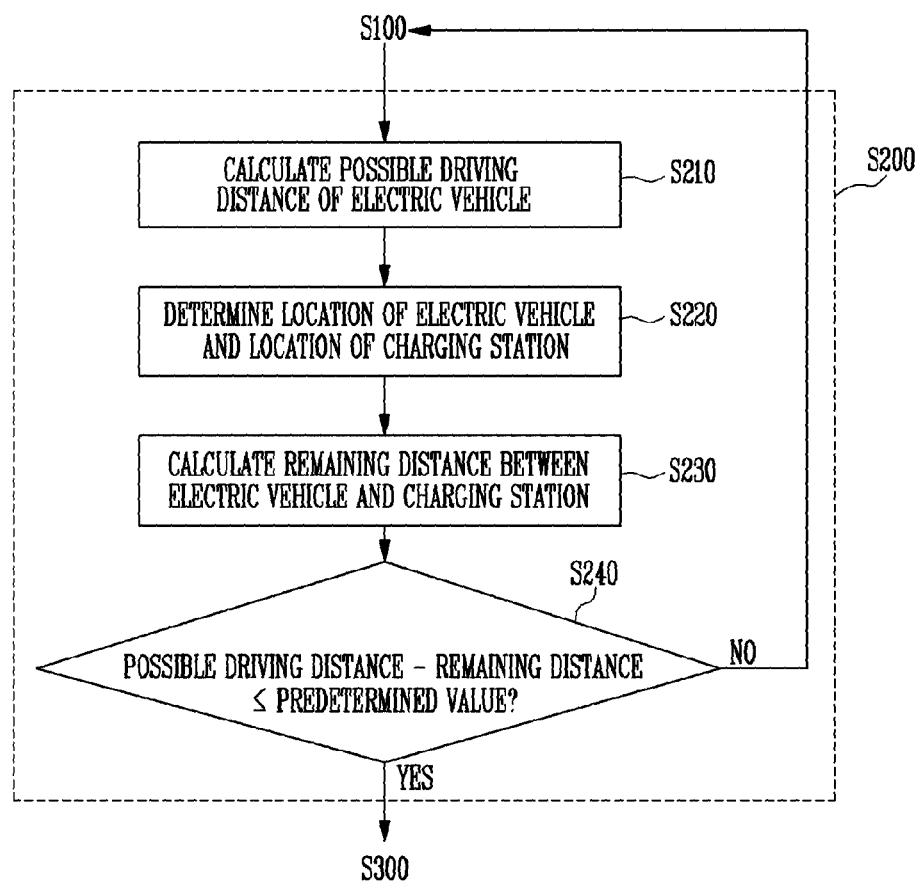

SYSTEM FOR CONTROLLING DRIVING OF ELECTRIC VEHICLE AND METHOD OF THE SAME

INCORPORATION BY REFERENCE TO ANY PRIORITY APPLICATIONS

The present application claims priority to and the benefit of Korean Patent Application No. 10-2014-0041232, filed on Apr. 7, 2014, in the Korean Intellectual Property Office, the entire contents of which are incorporated herein by reference in their entirety.

BACKGROUND

1. Field

The described technology generally relates to a system for controlling driving of an electric vehicle and a method of the same.

2. Description of the Related Technology

Despite the shortage of petroleum resources in the world, oil consumption is increasing and restrictions have been placed on the use of fossil fuels which produce pollution. Research has been conducted on electric powered vehicles in contrast to traditional automobiles which are powered by gasoline engines.

The standard electric vehicle has a driving motor that operates using power received from a rechargeable, or secondary, battery. Such electric vehicles may include a control function where the battery is not used when an under voltage protection (UVP) mode is activated due to the battery voltage decreasing to less than a predetermined level. When the UVP mode of the battery is activated, the electric vehicle cannot be driven.

SUMMARY OF CERTAIN INVENTIVE ASPECTS

One inventive aspect is a system for controlling driving of an electric vehicle and a method of the same to extend the maximum drivable distance of the electric vehicle.

Another aspect is a system for controlling driving of an electric vehicle including a remaining capacity calculator calculating remaining battery capacity and a controller controlling the magnitude of output current output to a driving unit of an electric vehicle to be a predetermined current limit value or less when the remaining battery capacity reaches a predetermined value.

The current limit value may be a current value enabling the electric vehicle to move a maximum distance.

A driving distance calculator may be further included. The driving distance calculator may calculate a possible driving distance of the electric vehicle when the electric vehicle is driven with the current limit value using the remaining battery capacity.

A navigation unit may be further included. The navigation unit may determine the location of the electric vehicle and the location of a peripheral charging station.

The controller may limit the magnitude of the output current to the current limit value when the remaining battery capacity reaches a level of remaining capacity enabling for driving to the charging station close to the electric vehicle.

The controller may calculate a remaining distance to the charging station using the location of the electric vehicle and the location of the charging station, and if the difference between a possible driving distance based on the remaining battery capacity and the remaining distance is within a predetermined value, the magnitude of the output current may be limited to the current limit value.

The navigation unit may further obtain information such as an altitude, a gradient, etc. of a route from the location of the electric vehicle to the location of the charging station.

The driving distance calculator may calculate the possible driving distance of the electric vehicle further using the information such as the altitude, the gradient, etc. of the route.

A weight measurement unit measuring a weight of the electric vehicle may be further included. The driving distance calculator may calculate the possible driving distance of the electric vehicle by considering the weight of the electric vehicle.

A display unit may be further included. The display unit may display at least one of the possible driving distance, the remaining distance and the remaining battery capacity.

The controller may send a call signal to a charging company or a towing company for the battery when the charging station is not found within the possible driving distance.

The call signal may include at least one of the current location of the electric vehicle and the location of the electric vehicle after the electric vehicle has moved the possible driving distance.

Another aspect is a method for controlling driving of an electric vehicle including calculating a remaining battery capacity, determining whether the remaining battery capacity has reached a predetermined value, and controlling a magnitude of an output current output to a driving unit of an electric vehicle to be a predetermined current limit value and less when the remaining battery capacity reaches the predetermined value.

When a remaining battery capacity of an electric vehicle falls to a predetermined value and less, the electric vehicle may be able to move a maximum distance.

The electric vehicle may also move to a charging station by finding a charging station near current location of the electric vehicle and limiting an output current.

Another aspect is a system for controlling driving of an electric vehicle including a motor, the system comprising a battery configured to output a driving current to the motor; a battery capacity calculator configured to determine the remaining battery capacity of the battery; and a controller configured to limit the driving current to a predetermined current limit value or less when the remaining battery capacity reaches a first predetermined value.

The current limit value can be a current value that enables the electric vehicle to travel a maximum distance. The system can further comprise a driving distance calculator configured to calculate an estimated maximum distance of the electric vehicle based on the remaining battery capacity and the current limit value. The system can further comprise a navigation unit configured to determine the location of the electric vehicle and the location of one or more nearby charging stations. The controller can be further configured to limit the driving current to the current limit value when the remaining battery capacity reaches a minimum capacity sufficient for the electric vehicle to reach the charging station. The controller can be further configured to i) calculate the remaining distance to the charging station based on the location of the electric vehicle and the location of the charging station and ii) limit the driving current to the current limit value when the difference between the estimated maximum distance and the remaining distance is less than a second predetermined value.

The navigation unit can be further configured to obtain information on the altitude and the gradient of a route between the location of the electric vehicle and the charging station. The driving distance calculator can be further configured to calculate the estimated maximum distance of the electric vehicle further based on the altitude and the gradient of the route. The system can further comprise a weight measurement unit configured to measure the weight of the electric vehicle, wherein the driving distance calculator is further configured to calculate the estimated maximum distance of the electric vehicle based on the measured weight of the electric vehicle. The system can further comprise a display unit configured to display at least one of the estimated maximum distance, the remaining distance and the remaining battery capacity. The controller can be configured to transmit a call signal to vehicle assistance service when the charging station is not found within the estimated maximum distance. The call signal can include at least one of the location of the electric vehicle and a predicted location of the electric vehicle based on the estimated maximum distance.

Another aspect is an electric vehicle comprising a motor; and a control system including: a battery configured to output a driving current to the motor; a battery capacity calculator configured to determine the remaining battery capacity of the battery; and a controller configured to limit the driving current to a predetermined current limit value when the remaining battery capacity is less than a threshold.

The control system can further include a driving distance calculator configured to calculate an estimated maximum distance of the electric vehicle based on the remaining battery capacity. The control system can further include a navigation unit configured to determine the location of the electric vehicle and the location of one or more charging stations within the estimated maximum distance from the location of the electric vehicle. The control system can further include a display configured to display the locations of the charging stations. The navigation unit can be further configured to obtain information on the altitude and the gradient of a plurality of routes between the electric vehicle and the respective charging stations and wherein the controller is further configured to select one of the charging stations based on the distances from the electric vehicle to the charging stations, the changes in altitude from the electric vehicle to the charging stations and the gradients of the of the routes between the electric vehicle and the charging stations. The driving distance calculator can be further configured to calculate the estimated maximum distance of the electric vehicle further based on the altitudes and the gradients of the routes. The controller can be further configured to limit the driving current to the predetermined value when the remaining battery capacity reaches a minimum capacity sufficient for the electric vehicle to reach at least one of the charging stations. The control system can further include a weight measurement unit configured to measure the weight of the electric vehicle and the driving distance calculator can be further configured to calculate the estimated maximum distance of the electric vehicle based on the measured weight of the electric vehicle.

BRIEF DESCRIPTION OF THE DRAWINGS

FIG. 3 is a view illustrating a method for controlling driving of an electric vehicle according to an embodiment.

DETAILED DESCRIPTION OF CERTAIN INVENTIVE EMBODIMENTS

Figure 1:
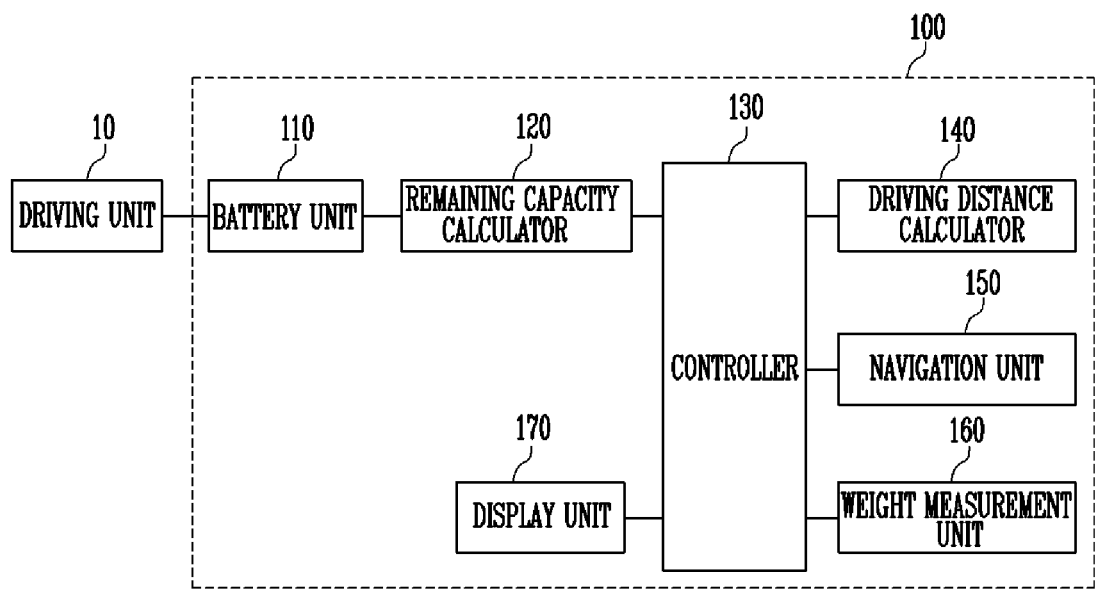
FIG. 1 is a block diagram illustrating a system for controlling driving of an electric vehicle according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the figures, dimensions may be exaggerated for the sake of clarity. It will be understood that when an element is referred to as being "between" two elements, it can be the only element between the two elements, or one or more intervening elements may also be present. Like reference numerals refer to like elements throughout.

Hereinafter, reference will now be made in detail to embodiments, examples of which are illustrated in the accompanying drawings. As used herein, the term "and/or" includes any and all combinations of one or more of the associated listed items.

FIG. 1 is a block diagram illustrating a system for controlling driving of an electric vehicle according to an embodiment.

Referring to FIG. 1, the system 100 for controlling an electric vehicle includes a battery unit or battery 110, a remaining battery capacity calculator or battery capacity calculator 120, a controller 130, a driving distance calculator 140, a navigation unit 150, a weight measurement unit 160 and a display unit 170.

The battery unit 110 can store power and supply the stored power to a driving unit 10 of the electric vehicle. The battery unit 110 can include at least one battery cell. Various secondary batteries capable of being charged can be used for the battery cell. For example, the secondary battery used for the battery cell may include at least one of a nickel-cadmium battery, a lead storage battery, a nickel metal hydride (NiMH) battery, a lithium battery, a lithium polymer battery, etc. When a charging device is connected to the battery unit 110, the battery cell can be charged by an external power source.

The driving unit 10 of the electric vehicle may be a motor. The electric vehicle can be driven via the motor.

The remaining battery capacity calculator 120 calculates the remaining capacity of the battery unit 110. The remaining capacity may be a state of charge (SOC) input from a battery management system (BMS) included in the battery unit 110 or a state of health (SOH).

The controller 130 can control the magnitude of the output power output to the driving unit 10 of the electric vehicle to a predetermined current limit value or less when the remaining battery capacity calculated by the remaining battery capacity calculator 120 reaches or falls below a predetermined value.

The current limit value may refer to a current value at which the electric vehicle can travel the greatest distance.

Generally, the greater the magnitude of the current output from the battery unit 110, the faster the speed of the motor, however this can cause the battery unit 110 to be discharged quickly. Also, the driving efficiency of the motor can decrease when the magnitude of the current output from the battery unit 110 increases. As a result, the maximum possible driving distance can be reduced when the motor is driven with currents that have increasing magnitudes. That is, depending on the magnitude of the output current or driving current supplied from the battery unit 110, the distance that the electric vehicle can travel may vary. In order for the electric vehicle to travel the maximum distance, the current output from the battery unit 110 should be controlled to be a predetermined value or less. The current limit value that can enable the electric vehicle to travel the maximum distance can be predetermined via use of experimental data.

When the remaining battery capacity reaches the predetermined value (e.g., about 20% of the remaining battery capacity), the controller 130 may limit the output current to the current limit value such that the electric vehicle can travel the maximum distance. When a driver attempts to accelerate the electric vehicle by requesting an output current that is above the current limit value by stepping on the accelerator, etc., the controller 130 can control the output current to be limited to the current limit value, and thus the speed of the electric vehicle is maintained at a certain speed or less.

The driving distance calculator 140 can calculate the possible driving distance or estimated maximum distance of the electric vehicle with the current limit value using the remaining battery capacity of the battery unit 110.

In some embodiments, the navigation unit 150 determines the location of the electric vehicle including the battery unit 110 and the location of at least one charging station near the electric vehicle. The navigation unit 150 can be a digital mapping device including a global positioning system (GPS), an altitude sensor and a navigational system. The navigation unit 150 can generate the current position coordinates including altitude based on a GPS signal using a digital map. Also, the position coordinate information of the charging station capable of charging the electric vehicle can be pre-stored.

In some embodiments, the navigation unit 110 calculates the location of a plurality of charging stations near the electric vehicle. In these embodiments, the controller 130 selects one of the charging stations for the electric vehicle to drive to based on, for example, the distance from the electric vehicle to the charging stations, the change in altitude from the electric vehicle to the charging stations, the gradient of the route between the electric vehicle and the charging stations and/or whether the charging stations are near a predetermined route of the electric vehicle. In other embodiments, the controller 130 display the locations of the charging stations to the driver of the vehicle via the display unit 170 such that the driver can select one of the charging stations to drive to.

In an embodiment, the controller 130 calculates the remaining distance to the charging station using the location of the electric vehicle and the location of the charging station. The controller 130 can also limit the magnitude of the output current to the current limit value when the difference between the possible driving distance of the electric vehicle calculated by the driving distance calculator 140 and the remaining distance is less than a predetermined value.

When there is enough remaining battery capacity in the battery unit 110 for the electric vehicle to reach the charging station, the magnitude of the output current can be limited to the current limit value to prevent the electric vehicle from being unable to move due to the battery unit 110 being completely discharged, thereby ensuring the battery unit 110 can reach the charging station to be recharged.

In an embodiment, the navigation unit 150 can obtain further information such as an altitude, a gradient, a distance on a map, etc. of the route from the location of the electric vehicle to the location of the charging station.

When there are many slopes on the route from the current location to the charging station, the possible driving distance that the electric vehicle can travel may be reduced. The driving distance calculator 140 can calculate the possible driving distance of the electric vehicle using the information such as the altitude, gradient, etc. on the route. If there are many slopes on the route (i.e. a large number of increases in elevation), the possible driving distance calculated by the driving distance calculator 140 may be reduced. If there are many down hills (i.e. a large number of reductions in elevation), the possible driving distance calculated by the driving distance calculator 140 may increase.

The weight measurement unit 160 can measure the weight of the electric vehicle. The entire weight of the electric vehicle can change according to the load being carried in the trunk of the electric vehicle and the number of passengers riding in the electric vehicle. The weight measurement unit 160 can include a weight measurement sensor mounted on each seat and in the trunk of the electric vehicle.

The heavier the weight of the electric vehicle, the shorter the possible driving distance. The driving distance calculator 140 can calculate the possible driving distance in consideration of the weight measured by the weight measurement unit 160.

The display unit 160 can display the possible driving distance and the remaining distance to the charging station of the electric vehicle calculated by the driving distance calculator 140 to a driver based on the control of the controller 130. The display unit 160 can also display information relating to the control mode when the magnitude of the output current of the battery unit 110 is controlled or limited to the current limit value when the remaining battery capacity reaches the predetermined value.

In one embodiment, if a charging station is not found within the possible driving distance based on the remaining battery capacity of the battery unit 110, the controller 130 may prepare for suspension of electric vehicle driving by transmitting a call signal to a vehicle assistance service such as a battery charging company or a car towing company.

The call signal may include at least one of the current location of the electric vehicle and the predicted location of the electric vehicle after the electric vehicle has traveled the possible driving distance.

Figure 2:
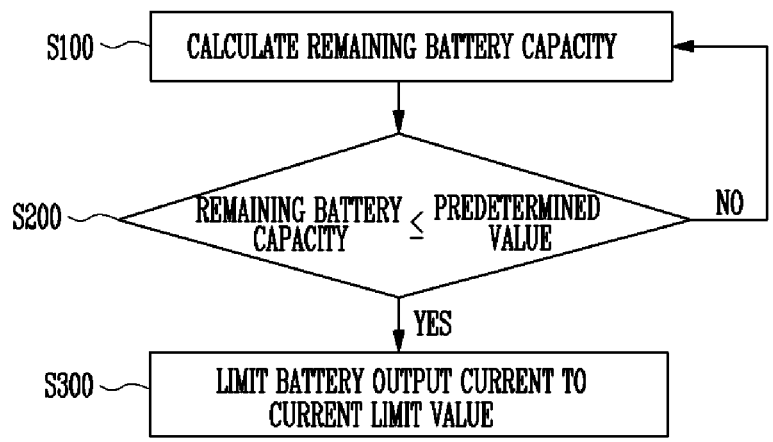
FIG. 2 is a flow chart illustrating a method for controlling driving of an electric vehicle according to an embodiment.

FIG. 2 is a flow chart illustrating a method for controlling driving of an electric vehicle according to an embodiment.

Referring to FIG. 2, the method for controlling driving of an electric vehicle calculates the remaining battery capacity of a battery unit 110 (S100). The remaining battery capacity of the battery unit 110 can be the SOC output from a battery management system included in the battery unit 110.

The controller 130 determines if the remaining battery capacity has reached a predetermined value (S200).

The controller 130 can control the magnitude of an output current output to a driving unit 10 of an electric vehicle to a predetermined current limit value or less when the remaining battery capacity is less than or substantially equal to a predetermined value (S300).

The current limit value refers to a current value that enables the electric vehicle to travel a maximum distance.

The controller 130 can ensure that the electric vehicle is able to travel the maximum distance by limiting the output current to the current limit value when the remaining battery capacity reaches the predetermined value (e.g., about 20% of the remaining battery capacity).

The controller 130 recalculates the remaining battery capacity when the remaining battery capacity is greater than the predetermined value (S100).

FIG. 3 is a view illustrating a method for controlling driving of an electric vehicle according to an embodiment.

FIG. 3 illustrates S200 shown in FIG. 2 in greater detail.

Referring to FIG. 3, the driving distance calculator 140 calculates the possible driving distance of the electric vehicle when the electric vehicle is driven with the current limit value using the remaining battery capacity of the battery unit 110 (S210).

The navigation unit 150 determine the location of the electric vehicle and the location of one or more of the nearest charging stations (S220).

The controller 130 calculates the remaining distance from the electric vehicle to the charging station (S230).

The controller 130 determines if the difference between the possible driving distance of the electric vehicle based on the remaining battery capacity and the remaining distance is less than or substantially equal to a predetermined value (S240).

When the difference between the possible driving distance and the remaining distance is less than or substantially equal to the predetermined value, the magnitude of the output current that is output to the driving unit 10 of the electric vehicle is controlled in step S300 in FIG. 2 to be limited to the predetermined current limit value.

As described above, when the remaining battery capacity falls to less than or substantially equal to the predetermined value, the electric vehicle can be controlled to ensure that the electric vehicle can travel the maximum distance. Also, the electric vehicle can travel to a charging station by locating the charging station near the current location of the electric vehicle and limiting the output current.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A system for controlling driving of an electric vehicle including a motor, the system comprising:
   a battery configured to output a driving current to the motor;
   a battery capacity calculator configured to determine the remaining battery capacity of the battery; and
   a controller configured to limit the driving current to a predetermined current limit value or less when the remaining battery capacity reaches a first predetermined value.

2. The system of claim 1, wherein the current limit value is a current value that enables the electric vehicle to travel a maximum distance.

3. The system of claim 2, further comprising:
   a driving distance calculator configured to calculate an estimated maximum distance of the electric vehicle based on the remaining battery capacity and the current limit value.

4. The system of claim 3, further comprising:
   a navigation unit configured to determine the location of the electric vehicle and the location of one or more nearby charging stations.

5. The system of claim 4, wherein the controller is further configured to limit the driving current to the current limit value when the remaining battery capacity reaches a minimum capacity sufficient for the electric vehicle to reach the charging station.

6. The system of claim 5, wherein the controller is further configured to i) calculate the remaining distance to the charging station based on the location of the electric vehicle and the location of the charging station and ii) limit the driving current to the current limit value when the difference between the estimated maximum distance and the remaining distance is less than a second predetermined value.

7. The system of claim 4, wherein the navigation unit is further configured to obtain information on the altitude and the gradient of a route between the location of the electric vehicle and the charging station.

8. The system of claim 7, wherein the driving distance calculator is further configured to calculate the estimated maximum distance of the electric vehicle further based on the altitude and the gradient of the route.

9. The system of claim 3, further comprising a weight measurement unit configured to measure the weight of the electric vehicle, wherein the driving distance calculator is further configured to calculate the estimated maximum distance of the electric vehicle based on the measured weight of the electric vehicle.

10. The system of claim 4, further comprising a display unit configured to display at least one of the estimated maximum distance, the remaining distance and the remaining battery capacity.

11. The system of claim 4, wherein the controller is configured to transmit a call signal to vehicle assistance service when the charging station is not found within the estimated maximum distance.

12. The system of claim 11, wherein the call signal includes at least one of the location of the electric vehicle and a predicted location of the electric vehicle based on the estimated maximum distance.

13. An electric vehicle, comprising:
   a motor; and
   a control system including:
      a battery configured to output a driving current to the motor;
      a battery capacity calculator configured to determine the remaining battery capacity of the battery; and
      a controller configured to limit the driving current to a predetermined current limit value when the remaining battery capacity is less than a threshold.

14. The electric vehicle of claim 13, wherein the control system further includes a driving distance calculator configured to calculate an estimated maximum distance of the electric vehicle based on the remaining battery capacity.

15. The electric vehicle of claim 14, wherein the control system further includes a navigation unit configured to determine the location of the electric vehicle and the location of one or more charging stations within the estimated maximum distance from the location of the electric vehicle.

16. The electric vehicle of claim 15, wherein the control system further includes a display configured to display the locations of the charging stations.

17. The electric vehicle of claim 15, wherein the navigation unit is further configured to obtain information on the altitude and the gradient of a plurality of routes between the electric vehicle and the respective charging stations and wherein the controller is further configured to select one of the charging stations based on the distances from the electric vehicle to the charging stations, the changes in altitude from the electric vehicle to the charging stations and the gradients of the of the routes between the electric vehicle and the charging stations.

18. The electric vehicle of claim 17, wherein the driving distance calculator is further configured to calculate the estimated maximum distance of the electric vehicle further based on the altitudes and the gradients of the routes.

19. The electric vehicle of claim 15, wherein the controller is further configured to limit the driving current to the predetermined value when the remaining battery capacity reaches a minimum capacity sufficient for the electric vehicle to reach at least one of the charging stations.

20. The electric vehicle of claim 14, wherein the control system further includes a weight measurement unit configured to measure the weight of the electric vehicle and wherein the driving distance calculator is further configured to calculate the estimated maximum distance of the electric vehicle based on the measured weight of the electric vehicle.

* * * * *